(12) United States Patent
Lin

(10) Patent No.: US 10,342,874 B2
(45) Date of Patent: Jul. 9, 2019

(54) GLUCOSAMINE PEPTIDE COMPOUNDS FOR TREATING LIVER METABOLIC DISORDERS

(71) Applicant: Far Eastern Memorial Hospital, New Taipei (TW)

(72) Inventor: Yu-Cheng Lin, New Taipei (TW)

(73) Assignee: FAR EASTERN MEMORIAL HOSPITAL, New Taipei (TW)

( * ) Notice: Subject to any disclaimer, the term of this patent is extended or adjusted under 35 U.S.C. 154(b) by 0 days.

(21) Appl. No.: 15/957,322

(22) Filed: Apr. 19, 2018

(65) Prior Publication Data

US 2019/0125873 A1 May 2, 2019

(30) Foreign Application Priority Data

Oct. 28, 2017 (TW) .............................. 106137272 A

(51) Int. Cl.

| A61K 47/18 | (2017.01) |
|---|---|
| A61K 31/558 | (2006.01) |
| A61K 31/726 | (2006.01) |
| A61K 38/04 | (2006.01) |
| A61K 47/08 | (2006.01) |
| A61K 47/42 | (2017.01) |
| A61P 1/16 | (2006.01) |

(52) U.S. Cl.
CPC ............ *A61K 47/18* (2013.01); *A61K 31/558* (2013.01); *A61K 31/726* (2013.01); *A61K 38/04* (2013.01); *A61K 47/08* (2013.01); *A61K 47/42* (2013.01); *A61P 1/16* (2018.01)

(58) Field of Classification Search
CPC ...... A61K 47/18; A61K 31/558; A61K 47/42; A61K 38/04; A61K 47/08; A61K 31/726; A61P 1/16
USPC ......................................... 435/6.11; 436/501
See application file for complete search history.

(56) References Cited

U.S. PATENT DOCUMENTS

| 4,357,322 A | 11/1982 | Rooks, II |
| 2011/0053167 A1* | 3/2011 | Holvoet ............... C12Q 1/6883 435/6.11 |
| 2013/0143826 A1* | 6/2013 | Liu ...................... A61K 31/337 514/21.9 |

FOREIGN PATENT DOCUMENTS

| CN | 103550230 A | 2/2014 |
| CN | 104288164 A | 1/2015 |

OTHER PUBLICATIONS

Glossary of medical education terms, Institute of International Medical Education. http://www.iime.org/glossary.htm Accessed in Mar. 2013. (Year: 2013).*
Cavallari et al. Muramyl Dipeptide-Based Postbiotics Mitigate Obesity-Induced Insulin Resistance via IRF4. Cell Metabolism 25, 1063-1074, May 2, 2017. (Year: 2017).*
Office Action dated Jun. 5, 2018 in corresponding TW Application No. 106137272 and English translation thereof, 10 pages.
Hamed Gitzad Kohan et al., "Synthesis and Characterization of a New Peptide Prodrug of Glucosamine with Enhanced Gut Permeability," PLoS One, 10(5), e0126786, https://doi.org/10.1371/journal.pone.0126786, May 15, 2015, pp. 1-14.

* cited by examiner

*Primary Examiner* — Yih-Horng Shiao
(74) *Attorney, Agent, or Firm* — Muncy, Geissler, Olds & Lowe, P.C.

(57) ABSTRACT

A glucosamine peptide compound or a pharmaceutically acceptable salt thereof are useful for treating liver metabolic disorders, wherein the glucosamine peptide compound may have the structure of Glc-L-Pep, and wherein Glc represents glucosamine moiety, L represents a linker, Pep represents a peptide moiety consisting of two to six amino acid residues, Glc and L are bonded by an ether linkage, and L and Pep are bonded by an amide linkage. The liver metabolic disorders include nonalcoholic fatty liver disease, nonalcoholic steatohepatitis, alcoholic fatty liver disease, alcoholic steatohepatitis, hepatic steatosis, liver fibrosis, cirrhosis or a combination thereof.

6 Claims, 15 Drawing Sheets

GLUCOSAMINE PEPTIDE COMPOUNDS FOR TREATING LIVER METABOLIC DISORDERS

CROSS-REFERENCE TO RELATED APPLICATION

This application claims the priority benefits of Taiwan Patent Application No. 106137272, filed on Oct. 28, 2017, the entirety of which is hereby incorporated by reference herein and made a part of this specification.

BACKGROUND

1. Field of the Invention

Disclosed is a glucosamine peptide compound or a pharmaceutically acceptable salt thereof for treating liver metabolic disorders, comprising nonalcoholic fatty liver disease (NAFLD), nonalcoholic steatohepatitis (NASH), alcoholic fatty liver disease (AFLD), alcoholic steatohepatitis (ASH), hepatic steatosis, liver fibrosis, cirrhosis, abetalipoproteinemia, hypobetalipoproteinemia, lipodystrophy, Weber-Christian disease, total parenteral nutrition associated liver disease, familial combined hyperlipidemia, glycogen storage disease, lysosomal acid lipase deficiency, Wolman disease, acute fatty liver of pregnancy or a combination thereof.

2. Description of Related Arts

Liver metabolic disorders, including but not limited to lipid metabolic disorders of liver, are highly associated with obesity, dyslipidemia, diabetes, and hypertension. Some common diseases associated to lipid metabolic disorders of liver include nonalcoholic fatty liver disease, nonalcoholic steatohepatitis, alcoholic fatty liver disease, alcoholic steatohepatitis, hepatic steatosis, liver fibrosis, and cirrhosis. It is known that people with metabolic disorders are more susceptible to fatty liver disease.

Fatty liver disease, which is the major cause of liver diseases globally, is related to obesity and overnutrition; the global prevalence rate is about 25% and up to 27.4% in Asia.

Generally, fatty liver refers to fat weight accounting for 5% or above of liver weight or steatosis observed in at least 30% of hepatocytes histologically. Fatty liver may cause inflammation of liver and abnormal liver function index and may even lead to liver fibrosis and cirrhosis.

It is believed that maintaining a healthy lifestyle is helpful for alleviating fatty liver disease, including keeping normal body weight, healthy diet, and regular exercise. However, there is no FDA-approved medication so far that can cure diseases associated to lipid metabolic disorders of liver, such as fatty liver.

SUMMARY

In view of the foregoing, this invention provides a use of a glucosamine peptide compound or a pharmaceutically acceptable salt thereof in treating liver metabolic disorders.

Specifically, the glucosamine peptide compound may have a structure of Glc-L-Pep, wherein Glc represents a glucosamine moiety, L represents a linker, Pep represents a peptide moiety consisting of two to six amino acid residues, Glc and L are bonded by an ether linkage, and L and Pep are bonded by an amide linkage.

In one embodiment, the glucosamine moiety has an amino group acylated to form an amide bond.

Specifically, the acyl group is substituted by an alkyl group or an aryl group, such as by a $C_1$-$C_{12}$ alkyl or a $C_6$-$C_{10}$ aryl.

In one embodiment, one or more hydroxy groups of the glucosamine moiety is amino-substituted, thio-substituted, glycoside-substituted, glucosamine-substituted or acylated.

In various embodiments, the glucosamine peptide compound includes various compounds known to bind to nucleotide-binding oligomerization domain-containing protein 2 (NOD2) and has the formula Glc-L-Pep described above, such as various NOD2 ligands or agonists.

In various embodiments, the glucosamine peptide compound includes (4R)-4-[[(2S)-2-[[(2R)-2-[(2R,5S)-3-acetamido-2,5-dihydroxy-6-hydroxymethyl)oxan-4-yl]oxypropanoyl]amino]propanoyl]amino]-5-amino-5-oxopentanoic acid and its derivative meeting the conditions above.

In one embodiment, according to the glucosamine peptide compound, -L- is

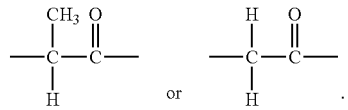

For example, in a preferred embodiment, -L- is

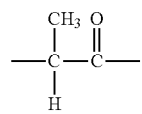

In one embodiment, according to the glucosamine peptide compound, Pep represents a peptide moiety consisting of two or three amino acid residues.

In a preferred embodiment, each amino acid residue is independently L-alanine, L-serine, D-isoglutamine, D-glutamine, D-glutamic acid or D-glutamate, D-aspartic acid or D-aspartate, or L-lysine.

In one embodiment, according to the glucosamine peptide compound, Pep is substituted by a lipophilic group.

In a preferred embodiment, the lipophilic group comprises a $C_{10}$-$C_{22}$ acyl group or a $C_1$-$C_{10}$ ester group.

In one embodiment, the glucosamine peptide compound has the structure below:

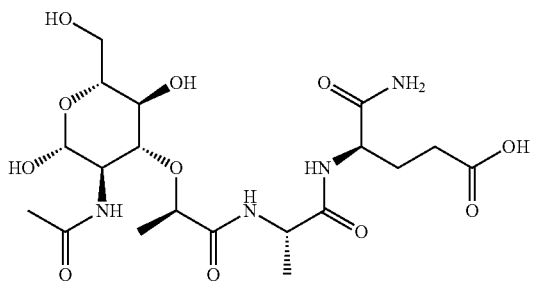 [SMILES: CC(=O)N[C@@H]1[C@@H](O[C@H](C)C(=O)N[C@@H](C)C(=O)N[C@H](CCC(=O)O)C(N)=O)[C@H](O)[C@@H](CO)O[C@H]1O]

(referred to as "Compound A").

In one embodiment, the glucosamine peptide compound has the structure below:

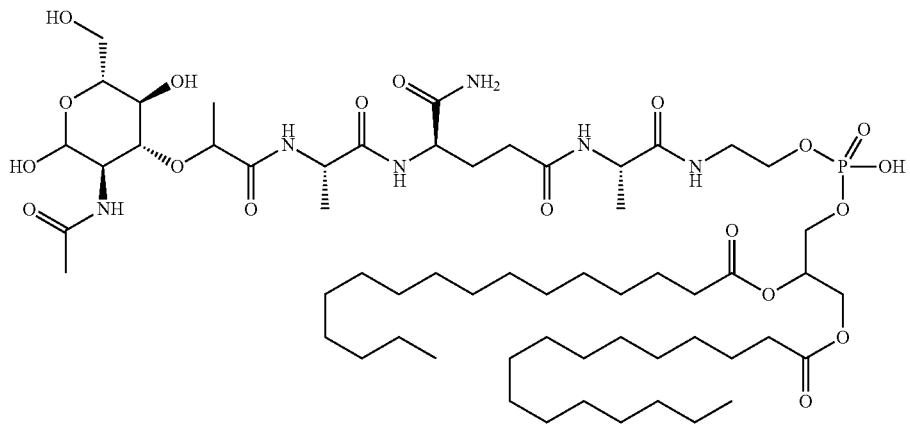 [SMILES: CCCCCCCCCCCCCCCC(=O)OCC(COP(=O)(O)OCCNC(=O)[C@H](C)NC(=O)CC[C@@H](NC(=O)[C@H](C)NC(=O)C(C)O[C@H]1[C@H](O)[C@@H](CO)OC(O)[C@@H]1NC(C)=O)C(N)=O)OC(=O)CCCCCCCCCCCCCCC]

(referred to as "Compound B").

In one embodiment, the glucosamine peptide compound has the structure below:

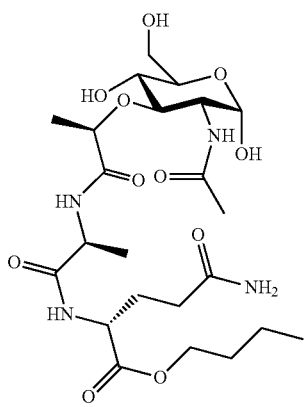

(referred to as "Compound C").

Specifically, examples of liver metabolic disorders include nonalcoholic fatty liver disease, nonalcoholic steatohepatitis, alcoholic fatty liver disease, alcoholic steatohepatitis, hepatic steatosis, liver fibrosis, cirrhosis or a combination thereof.

Specifically, examples of liver metabolic disorders include abetalipoproteinemia, hypobetalipoproteinemia, lipodystrophy, Weber-Christian disease, total parenteral nutrition associated liver disease, familial combined hyperlipidemia, glycogen storage disease, lysosomal acid lipase deficiency, Wolman disease, acute fatty liver of pregnancy or a combination thereof.

BRIEF DESCRIPTION OF THE DRAWINGS

FIG. 1A illustrates images of Oil Red O-stained HepG2 cells treated by different concentrations of Compound A, and FIG. 1B illustrates bar charts comparing number and size of lipid droplets;

FIG. 2A illustrates images of Oil Red O-stained HepG2 cells treated by Compound A for different durations, and FIG. 2B illustrates bar charts comparing number and size of lipid droplets;

FIG. 3A illustrates images of Oil Red O-stained HuH-7 cells treated by Compound A for different durations, and FIG. 3B illustrates bar charts comparing number and size of lipid droplets;

DETAILED DESCRIPTION OF EMBODIMENTS

Figure 1A:
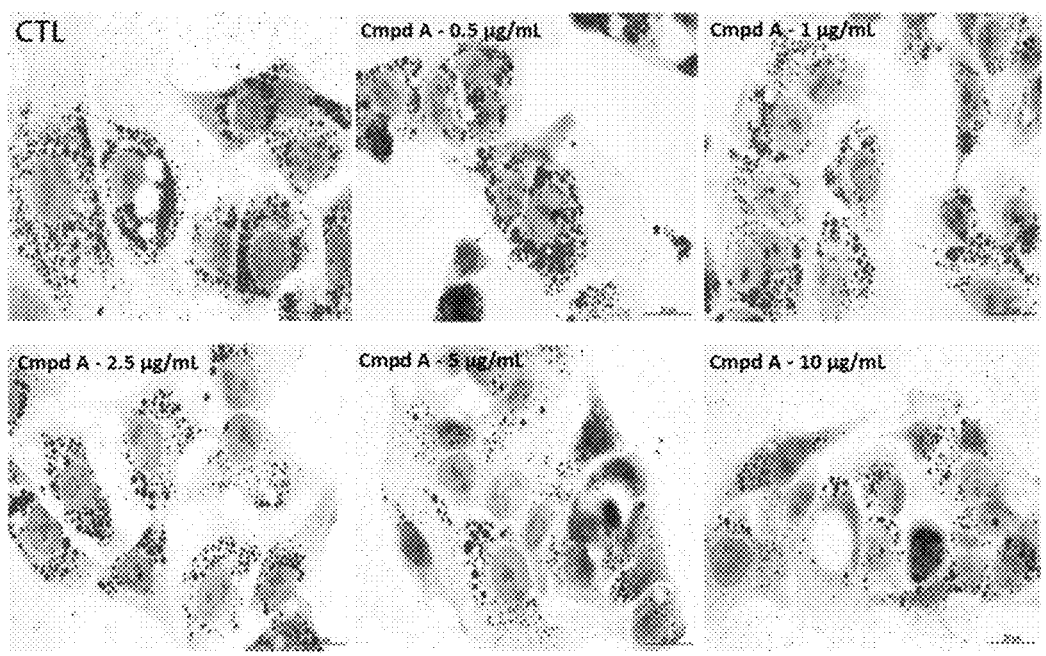
FIG. 1A and FIG. 1B illustrate Compound A decreasing lipid droplets in HepG2 cells in a dose-dependent manner.

To enable those skilled in the art to further appreciate the features and effects of the present disclosure, words and terms contained in the specification and appended claims are described and defined. Unless otherwise defined, all technical and scientific terms used herein have the same meaning as commonly understood by those of ordinary skill in the art to which this disclosure pertains. In the case of conflict, the present document and definitions contained herein will control.

As used herein, "a," "an" or similar expression is employed to describe elements and features of the present disclosure. This is done merely for convenience and to give a general sense of the scope of the present disclosure. Accordingly, this description should be read to include one or at least one and the singular also includes the plural unless it is obvious to mean otherwise.

As used herein, the term "comprises," "comprising," "includes," "including," "has," "having" or any other variant thereof is construed as an open-ended transitional phrase intended to cover a non-exclusive inclusion. For example, a composition or manufacture that comprises a list of elements is not necessarily limited to only those elements but may include other elements not expressly listed or inherent to such composition or manufacture. Further, unless expressly stated to the contrary, the term "or" refers to an inclusive or and not to an exclusive or. For example, a condition "A or B" is satisfied by any one of the following: A is true (or present) and B is false (or not present), A is false (or not present) and B is true (or present), and both A and B are true (or present). In addition, whenever open-ended transitional phrases are used, such as "comprises," "comprising," "includes," "including," "has," "having" or any other variant thereof, it is understood that transitional phrases such as "consisting essentially of" and "consisting of" are also disclosed and included.

In this disclosure, features or conditions presented as a numerical range or a percentage range, such as $C_1$-$C_8$, are merely for convenience and brevity. Therefore, a numerical range or a percentage range should be interpreted as encompassing and specifically disclosing all possible subranges and individual numerals or values therein, particularly all integers therein. For example, a range of "1 to 8" or "between 1 and 8" should be understood as explicitly disclosing all subranges such as 1 to 7, 2 to 8, 2 to 6, 3 to 6, 4 to 8, 3 to 8 and so on, particularly all subranges defined by integers, as well as disclosing all individual values such as 1, 2, 3, 4, 5, 6, 7 and 8. Unless otherwise defined, the aforesaid interpretation rule should be applied throughout the present disclosure regardless broadness of the scope.

Whenever amount, concentration or other numeral or parameter is expressed as a range, a preferred range or a series of upper and lower limits, it is understood that all ranges defined by any pair of the upper limit or preferred value and the lower limit or preferred value are specifically disclosed, regardless whether these ranges are explicitly described or not. In addition, unless otherwise defined, whenever a range is mentioned, the range should be interpreted as inclusive of the endpoints and every integers and fractions in the range.

Given the intended purposes and advantages of this disclosure are achieved, numerals or figures have the precision of their significant digits. For example, 40.0 should be understood as covering a range of 39.50 to 40.49.

As used herein, a Markush group or a list of items is used to describe examples or embodiments of the present disclosure. A skilled artisan will appreciate that all subgroups of members or items and individual members or items of the Markush group or list can also be used to describe the present disclosure. For example, when X is described as being "selected from a group consisting of $X_1$, $X_2$ and $X_3$," it is intended to disclose the situations of X is $X_1$ and X is $X_1$ and/or $X_2$. In addition, when a Markush group or a list of items is used to describe examples or embodiments of the present disclosure, a skilled artisan will understand that any subgroup or any combination of the members or items in the Markush group or list may also be used to describe the present disclosure. Therefore, when X is described as being "selected from a group consisting of $X_1$, $X_2$ and $X_3$" and Y is described as being "selected from a group consisting of $Y_1$, $Y_2$ and $Y_3$," the disclosure of any combination of X is $X_1$ and/or $X_2$ and/or $X_3$ and Y is $Y_1$ and/or $Y_2$ and/or $Y_3$.

The following embodiments and examples are illustrative in nature and are not intended to limit the present disclosure and its application. In addition, the present disclosure is not bound by any theory described in the background and summary above or the following embodiments or examples.

Generally, this invention relates to a use of a glucosamine peptide compound or a pharmaceutically acceptable salt thereof in treating liver metabolic disorders, such as the preparation of medicaments for treating liver metabolic disorders.

As used herein, the glucosamine peptide compound includes all peptide derivatives of glucosamine, such as peptide derivatives of 2-amino-2-deoxyglucose. In addition, the glucosamine may be modified or substituted, such as at the amino group to form N-acetylglucosamine, which may be further modified or substituted, such as by the formation of a ether linkage from the hydroxy group and a hydroxycarboxylic acid (e.g., 2-hydroxypropanoic acid) to form a carboxy-containing glucosamine compound, which has a carboxyl group reactive with the amino group at the N-terminal of a peptide to form an amide bond, so as to form the aforesaid glucosamine peptide compound.

For example, the glucosamine peptide compound may have a structure of Glc-L-Pep, wherein Glc represents a glucosamine moiety, L represents a linker, Pep represents a peptide moiety consisting of two to six amino acid residues, Glc and L are bonded by an ether linkage, and L and Pep are bonded by an amide linkage.

As used herein, liver metabolic disorders encompass various metabolic diseases of liver, primarily including lipid metabolic disorders of liver, examples comprising but not limited to nonalcoholic fatty liver disease, nonalcoholic steatohepatitis, alcoholic fatty liver disease, alcoholic steatohepatitis, hepatic steatosis, liver fibrosis, cirrhosis, abetalipoproteinemia, hypobetalipoproteinemia, lipodystrophy, Weber-Christian disease, total parenteral nutrition associated liver disease, familial combined hyperlipidemia, glycogen storage disease, lysosomal acid lipase deficiency, Wolman disease, acute fatty liver of pregnancy or a combination thereof. As used herein, fatty liver disease (FLD) includes, without limitation to, those caused by hepatitis, those caused by obesity, those caused by diabetes, those caused by insulin resistance and those caused by hypertriglyceridemia.

As used herein, pharmaceutically acceptable salts refer to ionic compounds, wherein active ingredients are modified to prepare their acid-addition salts or base-addition salts. One example of a pharmaceutically acceptable salt comprises an inorganic salt or organic salt containing amine as the basic group or an inorganic salt or organic salt containing carboxylic acid as the acidic group. Pharmaceutically acceptable salts may be prepared without undue experimentation by reference to "Pharmaceutical Salts: Properties, Selection, and Use", P. Heinrich Stahl and Camille G. Wermuth, published by John Wiley & Sons Inc, March 2011, which is incorporated by reference in its entirety.

On the other hand, pharmaceutically acceptable salts of the compounds disclosed in this invention may be made from parent compounds via conventional chemical synthesis, wherein the parent compounds contain a basic or acidic moiety. Generally, such salts may be prepared by reacting the free acid or base forms of these compounds with a stoichiometric amount of the appropriate base or acid in water, in an organic solvent, or in a mixture thereof; generally, non-aqueous media like ether, ethyl acetate, ethanol, isopropanol, or acetonitrile are preferred. Various examples of pharmaceutically acceptable salts are described in "Remington: The Science and Practice of Pharmacy", 21st edition, Lippincott, Williams & Wilkins, (2005), which is incorporated by reference in its entirety.

As used herein, the term "treatment" refers to obtaining desired pharmacological effects and/or physiological effects, including both prophylactic or preventative measures for completely or partially preventing a disease or symptom and therapeutic treatment for completely or partially curing a disease or providing counteracting effect against disease development.

As an example of the Glc-L-Pep structure, in one embodiment, any one or more of the glucosamine moiety, the linker and the peptide moiety shall meet one or more of the following conditions:

1) The glucosamine moiety may be modified; for example, the amino group may be acylated by $C_1$-$C_6$ alkyl, $C_1$-$C_{12}$ alkyl or $C_6$-$C_{10}$ aryl to form an amide bond. For example, the glucosamine moiety may be N-acetylglucosamine.

2) The linker and the glucosamine moiety are bonded via an ether linkage (—O—), and the linker and the peptide moiety are bonded via an amide linkage (—(C=O)—(NH)—). In addition, the linker preferably comprises both a hydroxyl group and a carboxyl group, such that an ether linkage can be formed by the hydroxyl group and the glucosamine moiety, and an amide linkage can be formed by the carboxyl group and the amino group at the N-terminal of the peptide moiety; as an example, the linker may be derived from a $C_1$-$C_6$ hydroxycarboxylic acid, such as

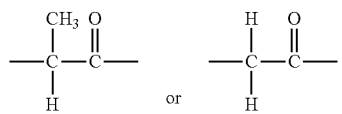

group, wherein the carbon atom at the left is bonded to the glucos amine moiety via ether linkage, and the carbon atom at the right is bonded to the peptide moiety via amide linkage. For example, the Glc-L-Pep structure may be a Glc-lactoyl-Pep structure.

3) The peptide moiety has two to six and preferably two or three amino acid residues, wherein each amino acid residue may be D-form or L-form and may be selected from glycine, alanine, valine, leucine, isoleucine, phenylalanine, tryptophan, tyrosine, aspartic acid, histidine, asparagine, glutamic acid, lysine, glutamine, isoglutamine, methionine, arginine, serine, threonine, cysteine and proline residues. Each amino acid residue is preferably L-alanyl, L-seryl, D-isoglutaminyl, D-glutaminyl, D-glutamyl, D-aspartyl, or L-lysyl. For example, the Glc-L-Pep structure may be represented as Glc-L-AA1-AA2, wherein AA1 is L-alanyl or L-seryl and AA2 is D-isoglutaminyl, D-glutaminyl, D-glutamyl or D-aspartyl. For example, the Glc-L-Pep structure may also be represented as Glc-L-AA1-AA2-AA3, wherein AA1 and AA2 are defined as above and AA3 is L-alanyl or L-lysyl.

The term "alkyl" refers to a straight chain or branch chain saturated hydrocarbonyl group, such as $C_1$-$C_{12}$ or $C_1$-$C_6$ hydrocarbonyl group; examples include methyl, ethyl, 1-propyl, 2-propyl, 1-butyl, 2-methyl-1-propyl (isobutyl, —$CH_2CH(CH_3)_2$), 2-butyl (sec-butyl, —$CH(CH_3)$ $CH_2CH_3$), 2-methyl-2-propyl (tert-butyl, —$C(CH_3)_3$), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl, but not limited thereto.

A hydroxyl group refers to a —OH radical; an amino group refers to a —$NH_2$ radical; and a thiol group refers to a —SH radical. An acyl group refers to a carbonyl moiety with a carbon atom bonded to other atoms. The carbon atom of the carbonyl group is bonded to a carbon atom of, for example, alkyl, aryl, aralkylcycloalkyl, cycloalkylalkyl, heterocyclyl, heterocyclylalkyl, heteroaryl, or heteroarylalkyl group.

An aryl refers to an aromatic carbocyclic group, which may be a single ring or a polycyclic system formed by rings fused together or linked by a covalent bond, and which may be substituted or unsubstituted. As used herein, examples of an aryl group include phenyl, naphthyl, and biphenylyl, but not limited thereto.

The peptide moiety is preferably composed by two or three amino acid residues; preferably, the first amino acid residue bonded to the linker via amide linkage is an L-form residue, such as L-alanyl or L-seryl. Preferably, the second amino acid residue is a D-form residue, such as D-isoglutaminyl, D-glutaminyl, D-glutamyl or D-aspartyl. If any, the third amino acid residue is preferably an L-form residue, such as L-alanyl or L-lysyl.

Preferably, the peptide moiety is substituted by a lipophilic group, such as at the second or third amino acid residue. The lipophilic group may be a $C_{10}$-$C_{22}$ acyl group or a $C_1$-$C_{10}$ ester group, preferably being a $C_{16}$-$C_{18}$ acyl group or a $C_2$-$C_6$ ester group, more preferably being a stearyl group, a palmitoyl group, a dipalmitoyl-phosphatidylethanolamine group or a butyl ester group. For example, the glucosamine moiety may be represented by Glc-L-Pep, wherein Pep has a terminal amino acid residue modified by phosphatidylethanolamine.

In one embodiment, fatty liver diseases include nonalcoholic fatty liver disease, nonalcoholic steatohepatitis, alcoholic fatty liver disease, alcoholic steatohepatitis and other diseases associated to lipid metabolic disorder in liver and leading to hepatic steatosis. In one embodiment, hepatic steatosis refers to over-accumulation of hepatic fat in liver tissues.

Unless otherwise specified, the glucosamine peptide compound or a pharmaceutically acceptable salt thereof can be in various forms, including powders for concentrate for dispersion for infusion, tablets, capsules, sachets, dragees, powders, granules, lozenges, powders for reconstitution, liquid preparations, or suppositories. In one embodiment, the glucosamine peptide compound or a pharmaceutically acceptable salt thereof is in the form of powders for concentrate for dispersion for infusion. In one embodiment, the glucosamine peptide compound or a pharmaceutically acceptable salt thereof is encapsulated by liposome.

Unless otherwise specified, the glucosamine peptide compound or a pharmaceutically acceptable salt thereof is administered in a therapeutically effective amount, which represents for example an amount of the active compound sufficient to elicit the desired therapeutic effect in a subject receiving the treatment. As understood by a person skilled in the art, the therapeutically effective amount may vary under different circumstances, factors including route of administration, use of excipient, and co-existence of other therapeutic treatment. "Guidance for Industry and Reviewers Estimating the Safe Starting Dose in Clinical Trials for Therapeutics in Adult Healthy Volunteers" published by the Food and Drug Administration of the United States Department of Health and Human Services has disclosed the way of calculating human equivalent dose (HED): HED=animal dose (mg/kg)*(animal weight (kg)/human weight (kg))$^{0.33}$.

EXAMPLES

Without limiting the scope of the present invention, exemplary instruments, apparatuses, processes and results according to various embodiments are described in detail below. It should be noted that titles or subtitles may be used in some embodiments to facilitate understanding and shall not be interpreted as limiting the subject matter described. While some theories may be proposed herein, the present disclosure is not bound by any theories described regardless of whether they are right or wrong, as long as the embodiments can be implemented according to the present disclosure.

Materials and statistical methods used in the embodiments are described below:

Major reagents: Compound A and Compound B are commercially available from Sigma Aldrich, and Compound C is commercially available from InvivoGen.

Compound A has a structure shown below:

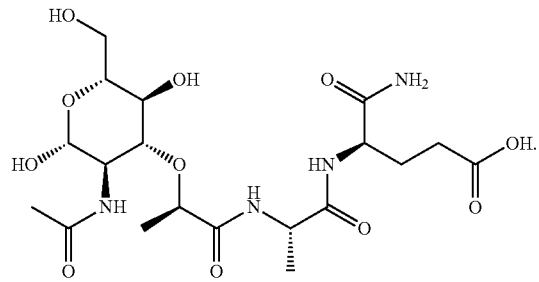 [SMILES: CC(=O)N[C@@H]1[C@@H](O[C@H](C)C(=O)N[C@@H](C)C(=O)N[C@H](CCC(=O)O)C(N)=O)[C@H](O)[C@@H](CO)O[C@H]1O]

Compound B has a structure shown below:

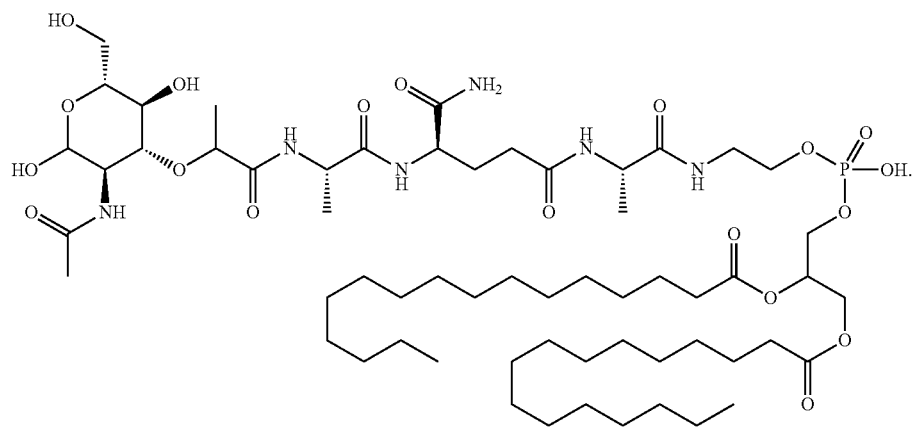 [SMILES: CCCCCCCCCCCCCCCC(=O)OCC(COP(=O)(O)OCCNC(=O)[C@H](C)NC(=O)CC[C@@H](NC(=O)[C@H](C)NC(=O)C(C)O[C@H]1[C@H](O)[C@@H](CO)OC(O)[C@@H]1NC(C)=O)C(N)=O)OC(=O)CCCCCCCCCCCCCCC]

Compound C has a structure shown below:

In addition to Compound A, Compound B, and Compound C, various glucosamine peptide compounds as defined above are also useful, such as various NOD2 ligands or agonists having the aforesaid Glc-L-Pep structure, such as muramyl dipeptides or derivatives thereof.

Cell culture: HepG2 (BCRC No. 60177) is available from the Bioresource Collection and Research Center (BCRC), and HuH-7 (JCRB0403) is available from the Japanese Collection of Research Bioresources (JCRB).

Mouse strain: 5-week-old C57BL/6JNarl male mice were purchased from the National Laboratory Animal Center (NLAC) in Taiwan.

Feed: available from Research Diets, including chow diet D12450B (fat as 10% of energy source) and high fat diet D12492 (fat as 60% of energy source, with cholesterol content adjusted to 1.25 wt %); the composition of each feed is shown below.

|  | Feed composition | | | |
|---|---|---|---|---|
|  | Chow Diet D12450B | | High Fat Diet D12492 | |
| Percentage | gm % | kcal % | gm % | kcal % |
| Protein | 19.2 | 20 | 26 | 20 |
| Carbohydrate | 67.3 | 70 | 26 | 20 |
| Fat | 4.3 | 10 | 35 | 60 |
| Kcal/gm | 3.85 | | 5.24 | |

Statistical analysis methods: data are represented by mean±SD; statistical analysis is performed using one-way ANOVA and Student's t test, wherein p-value less than 0.05 indicates statistical significance; p-value is illustrated as *<0.05, <0.01, *<0.001.

Example 1: Effect of Compound A on Lipid Droplet Formation in HepG2 Cells (I)

Human hepatocellular carcinoma cell line HepG2 was cultured in Dulbecco's modified Eagle's medium (DMEM, containing 4,500 mg/L D-glucose and L-glutamine) supplemented with 10% fetal bovine serum and 1% penicillin/streptomycin at 37° C. incubator with 5% $CO_2$. To induce in vitro fatty liver cell model on HepG2 with oleic acid-bovine serum albumin complex (Sigma-Aldrich, USA), HepG2 cells were cultured in a 24-well plate at a cell volume of $8\times10^4$; after 18 to 24 hours when a 70% confluence of cell growth has reached, 0.1 mM of oleic acid was added for culturing for 24 hours. After the replacement of culture medium containing oleic acid, 0.5 µg/mL, 1 µg/mL, 2.5 µg/mL, 5 µg/mL and 10 µg/mL of Compound A were added to DMEM containing 2% fetal bovine serum for culturing for 8 hours; each experimental group performed four repetitions.

Oil Red O (ORO) staining was used to confirm the level of lipid droplets, e.g., amount of red particles, in HepG2. After 24 hours of oleic acid treatment, HepG2 cells were fixed with 4% paraformaldehyde for 15 minutes, followed by phosphate-buffered saline (PBS) washing for three times and then ORO staining for 1 hour. After staining, the cells were washed with PBS for three times, followed by hematoxylin staining for 5 minutes. The coverslip was reversely placed on the slide and sealed with glycerine for observation with optical microscope; images were taken and saved as electronic files.

Intracellular lipid droplets were quantified by Image J (National Institutes of Health, NIH) after adjustment to a proper threshold value. Images with at least 20 cells were analyzed and quantified by Image J with the "analyze particles" functions in threshold single sections with size ($pixel^2$) setting from 0.1 to 10.

Figure 1B:
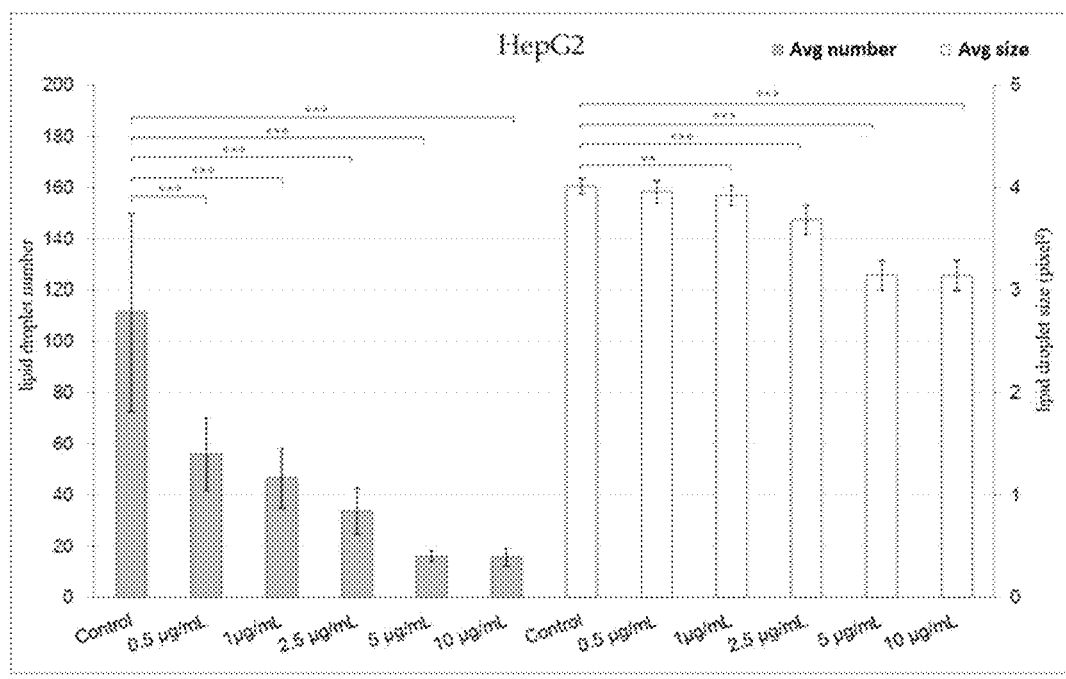

The results show that Compound A decreases lipid droplet accumulation in HepG2, and the level of lipid droplet accumulation is in negative correlation to the concentration of Compound A (FIG. 1A—scale bar: 20 µm, magnification: 1000×, 100× oil objective). The number and size of lipid droplets in HepG2 stained by ORO were quantified by Image J, the results showing that the number and size of lipid droplets decrease with the increase of Compound A concentration in a dose-dependent manner reaching statistical significance (FIG. 1B). Maximum reduction of lipid droplets in HepG2 occurs at a concentration of 5 µg/mL to 10 µg/mL of Compound A.

Example 2: Effect of Compound A on Lipid Droplet Formation in HepG2 Cells (II)

Similar to Example 1, to induce in vitro fatty liver cell model on HepG2 with oleic acid, HepG2 cells were cultured in a 24-well plate at a cell volume of $8\times10^4$ and added with 0.1 mM of oleic acid for 24-hour culturing. After the replacement of culture medium containing oleic acid, 10 µg/mL of Compound A was added to DMEM for culturing for 4 hours, 8 hours, 16 hours, and 24 hours; each time point performed four repetitions. ORO staining was used to confirm the level of lipid droplets in HepG2, and their number and size were quantified by Image J.

Figure 2A:
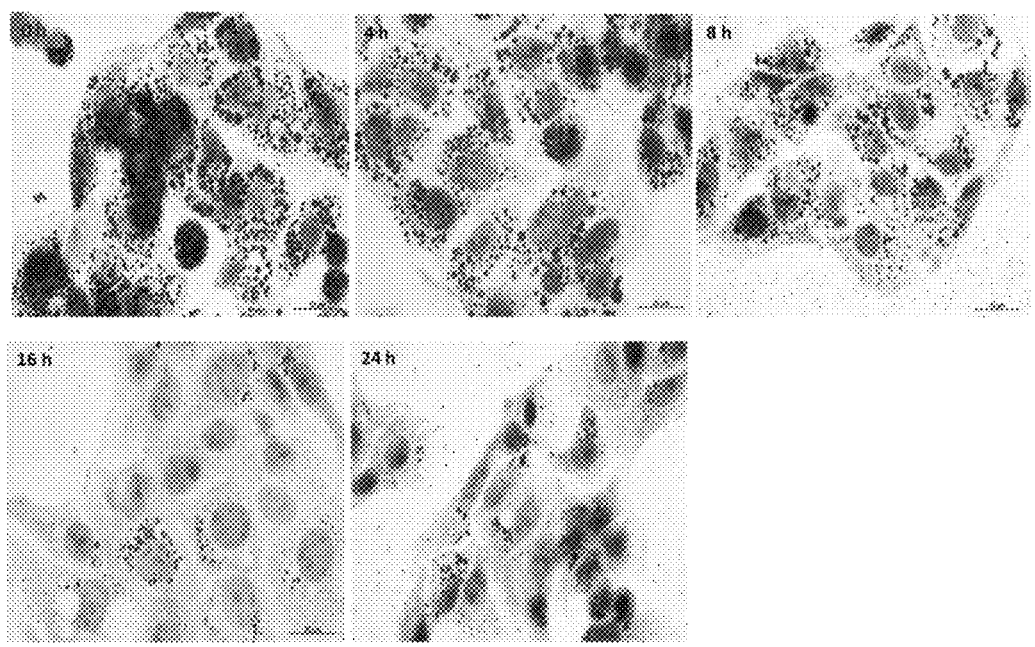
FIG. 2A and FIG. 2B illustrate Compound A decreasing lipid droplets in HepG2 cells in a time-dependent manner.
Figure 2B:
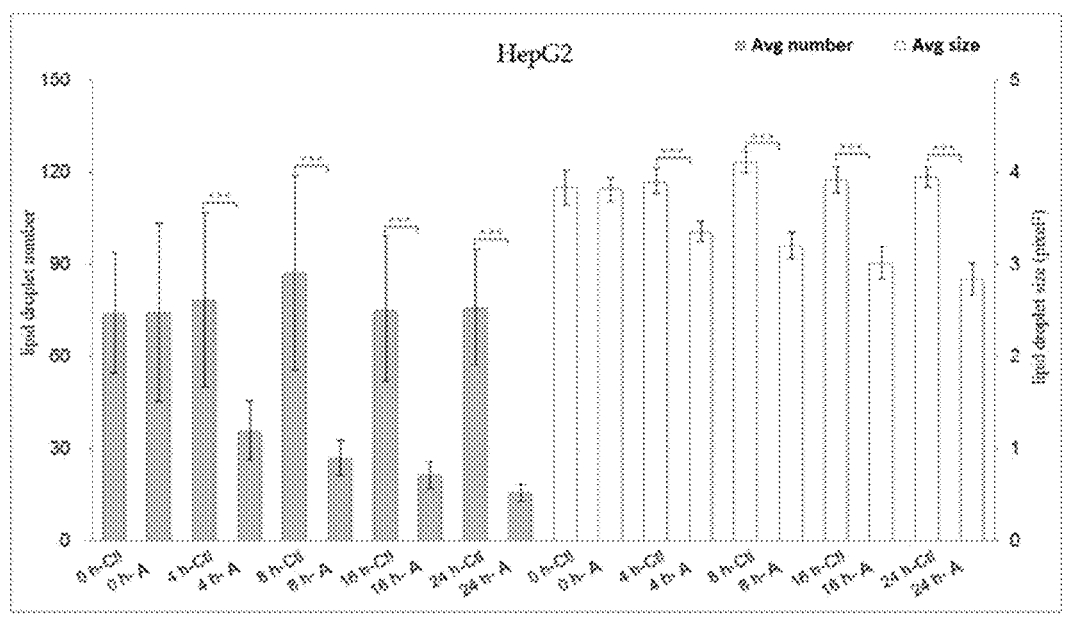

The results show that longer treatment time of Compound A results in less lipid droplet accumulation in HepG2 (FIG. 2A—scale bar: 20 µm, magnification: 1000×, 100× oil objective). The number and size of lipid droplets in HepG2 stained by ORO were quantified by Image J, the results showing that the number and size of lipid droplets decrease with the increase of treatment time of Compound A in a time-dependent manner reaching statistical significance (FIG. 2B). Significant reduction of lipid droplets in HepG2 can be observed after 4-hour treatment of Compound A, and maximum reduction occurs at 8-hour treatment.

Example 3: Effect of Compound A on Lipid Droplet Formation in HuH-7 Cells

Another human hepatocellular carcinoma cell line HuH-7 was used to test the temporal effect of Compound A to further confirm the effect of Compound A on intracellular lipid droplets. Similar to Example 2, to induce in vitro fatty liver cell model on HuH-7 with oleic acid, HuH-7 cells were cultured in a 24-well plate at a cell volume of $8\times10^4$ and added with 0.1 mM of oleic acid for 24-hour culturing. After the replacement of culture medium containing oleic acid, 10 µg/mL of Compound A was added to DMEM for culturing for 4 hours, 8 hours, 16 hours, and 24 hours; each time point performed four repetitions. ORO staining was used to confirm the level of lipid droplets in HuH-7, and their number and size were quantified by Image J.

Figure 3A:
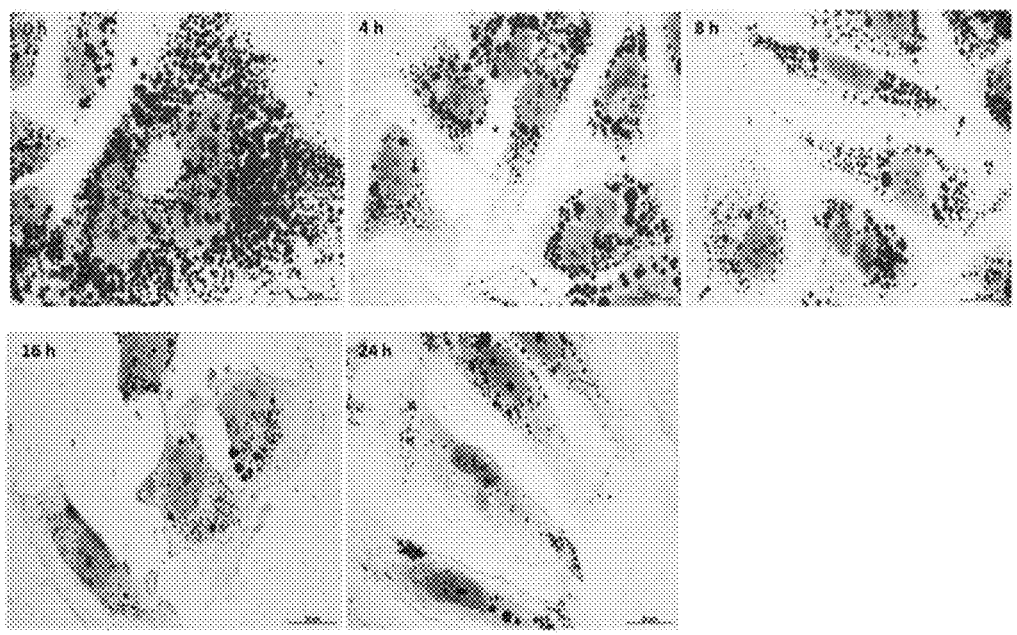
FIG. 3A and FIG. 3B illustrate Compound A decreasing lipid droplets in HuH-7 cells in a time-dependent manner.
Figure 3B:
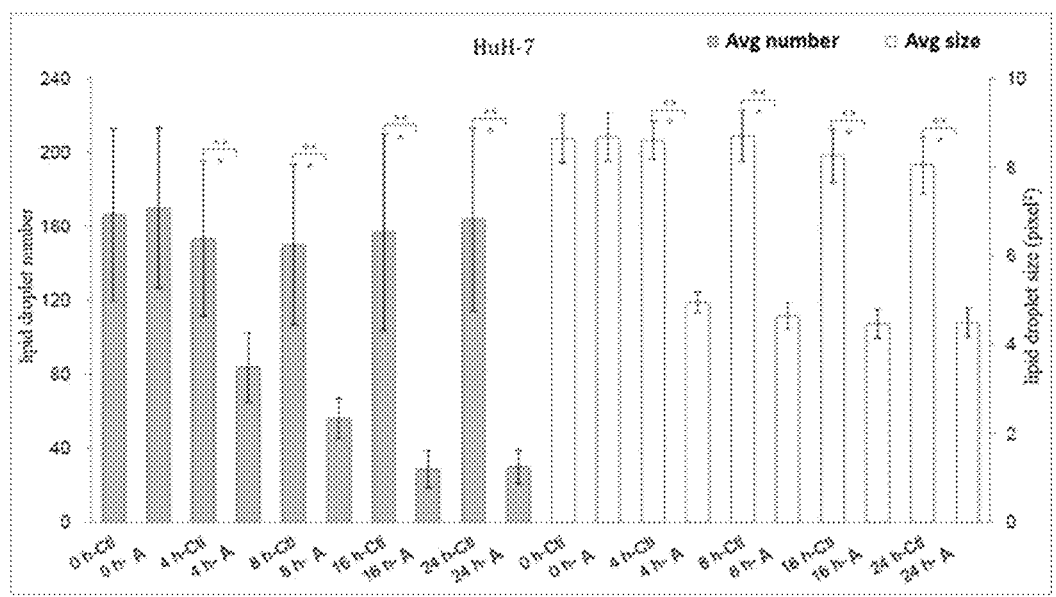

The results show that longer treatment time of Compound A results in less lipid droplet accumulation in HuH-7 (FIG. 3A—scale bar: 20 µm, magnification: 1000×, 100× oil objective). The number and size of lipid droplets in HuH-7 stained by ORO were quantified by Image J, the results showing that the number and size of lipid droplets decrease with the increase of treatment time of Compound A in a time-dependent manner reaching statistical significance (FIG. 3B). Significant reduction of lipid droplets in HuH-7 can be observed after 4-hour treatment of Compound A, and maximum reduction occurs at 16-hour treatment.

Example 4: Fatty Liver Animal Test

24 C57BL/6JNarl male mice at 5 weeks of age were purchased from the National Laboratory Animal Center and housed in the laboratory animal room of the Far Eastern Memorial Hospital at a constant temperature of 22° C., 55% humidity, automatic air regulation (ventilation rate of 12 times per hour), automatic light control (12:12 hour light/dark cycle), and provided with free access to water and chow diet D12450B (Research Diets, Inc.) for two weeks.

Then the 24 mice (7 weeks of age) were randomly divided into four groups, each containing six mice—Group 1 is the chow diet (CD) control group fed with chow diet D12450B; Group 2 is the high fat diet (HFD) group fed with high fat diet (i.e., modified D12492); Group 3 is the HFD+Compound A treatment group provided with high fat diet and Compound A; and Group 4 is the HFD+Compound B treatment group provided with high fat diet and Compound B.

Group 1 was fed with chow diet for 18 weeks, followed by 2 more weeks of chow diet, and then given an intraperitoneal injection of saline, without receiving Compound A or Compound B. Group 2, the HFD group, was fed with high fat diet for 18 weeks, followed by 2 more weeks of high fat diet, and then given an intraperitoneal injection of saline, without receiving Compound A or Compound B. Group 3, the HFD+Compound A treatment group, was fed with high fat diet for 18 weeks and then given an intraperitoneal injection of 2 mg/kg of Compound A per mouse, three times a week (once every one or two days) for two weeks, a total of six injections of Compound A. Group 4, the HFD+Compound B treatment group, was fed with high fat diet for 18 weeks and then given an intraperitoneal injection of 2 mg/kg of Compound B per mouse, three times a week (once every one or two days) for two weeks, a total of six injections of Compound B. After completion of feeding and treatment described above, the mice were weighed and euthanized with $CO_2$, and their blood and liver tissue specimens were collected for analysis.

Figure 4A:
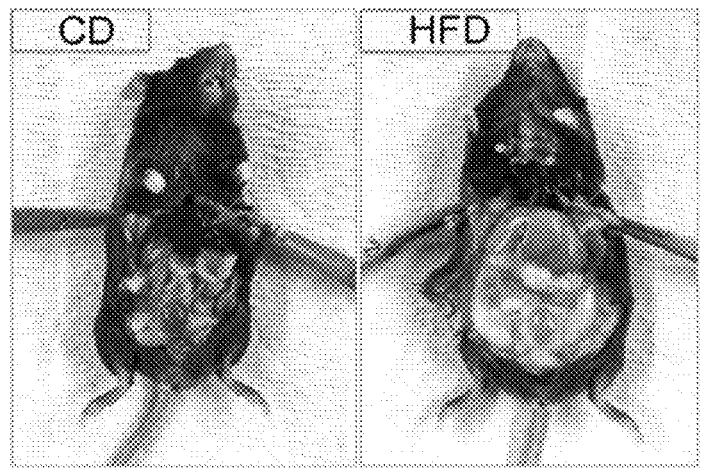
FIG. 4A illustrates anatomic images of mice fed with chow diet and high fat diet respectively.
Figure 4B:
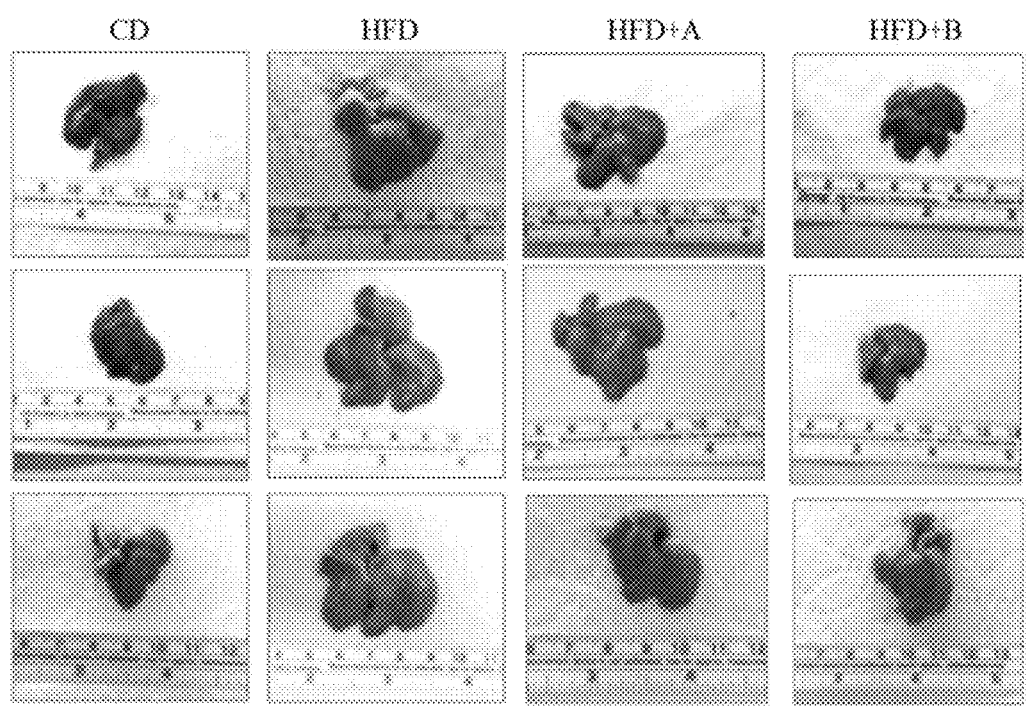
FIG. 4B illustrates appearance of liver.
Figure 4C:
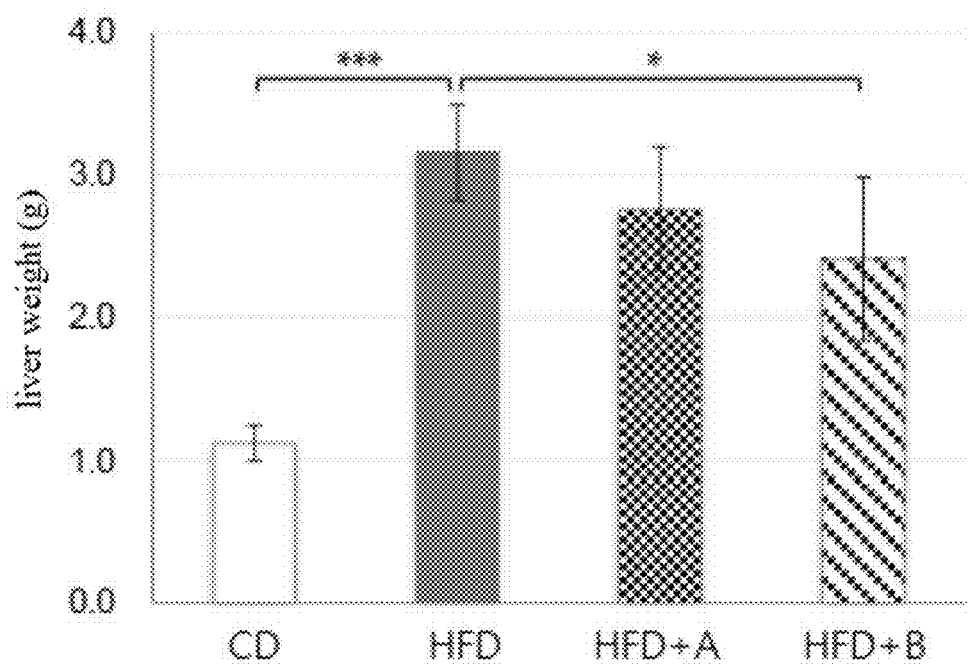
FIG. 4C illustrates liver weight analysis.
Figure 4D:
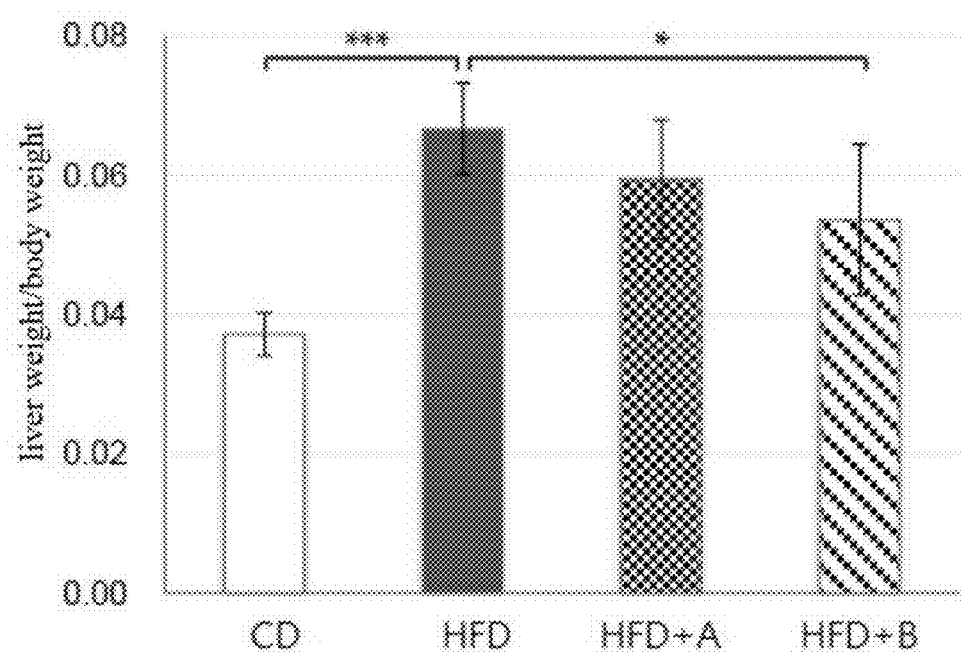
FIG. 4D illustrates weight ratio of liver to body weight.

It can be observed from the anatomical study that HFD-fed C57BL/6JNarl mice have much bigger size than CD-fed mice (FIG. 4A). Pictures of the liver appearance show that Group 1 has the smallest liver, Group 2 has the biggest liver, and both Group 3 and Group 4 have smaller livers than Group 2 (FIG. 4B). Statistical analysis of liver weight shows that the average liver weight of Group 2 is greater than Group 1, and the average liver weight of Group 4 is less than Group 2, both reaching statistical significance (FIG. 4C). To eliminate the effect of body weight difference of mice on liver weight change, the ratio of liver weight to body weight is further calculated, and the results show that Group 2 has a greater average liver weight percentage than Group 1, and Group 4 has a smaller average liver weight percentage than Group 2, both reaching statistical significance (FIG. 4D).

Example 5: Blood Biochemistry

Blood samples from mice of each group in Example 4 were tested for measurement of serum aspartate transaminase (AST), alanine transaminase (ALT), total cholesterol (T-CHO), triglyceride (TG) and glucose (GLU). AST and ALT are common measures of liver function.

the analysis above may be used to evaluate the effect of high fat diet, Compound A and Compound B on fatty liver disease.

Figure 5A:
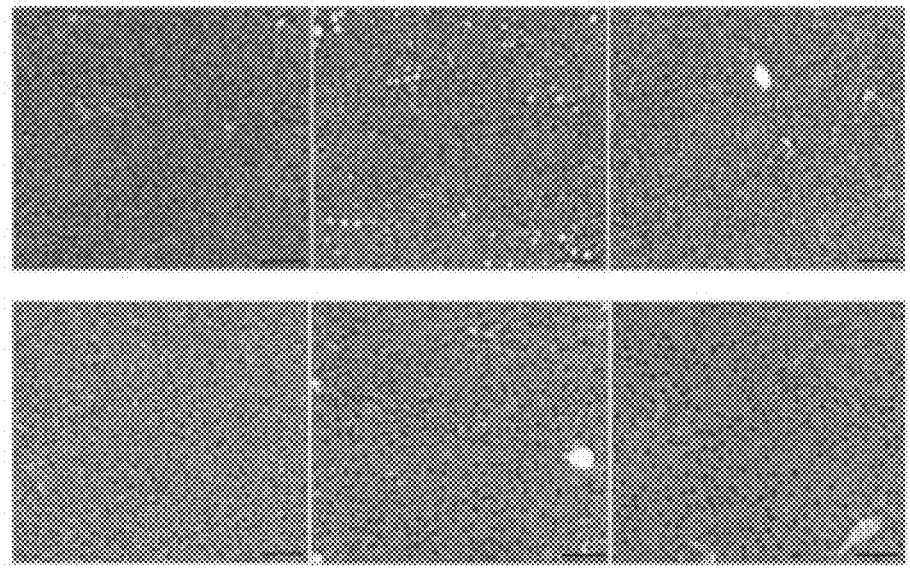
FIG. 5A through FIG. 5D illustrate H&E stain images of liver tissue from each mice group.
Figure 5B:
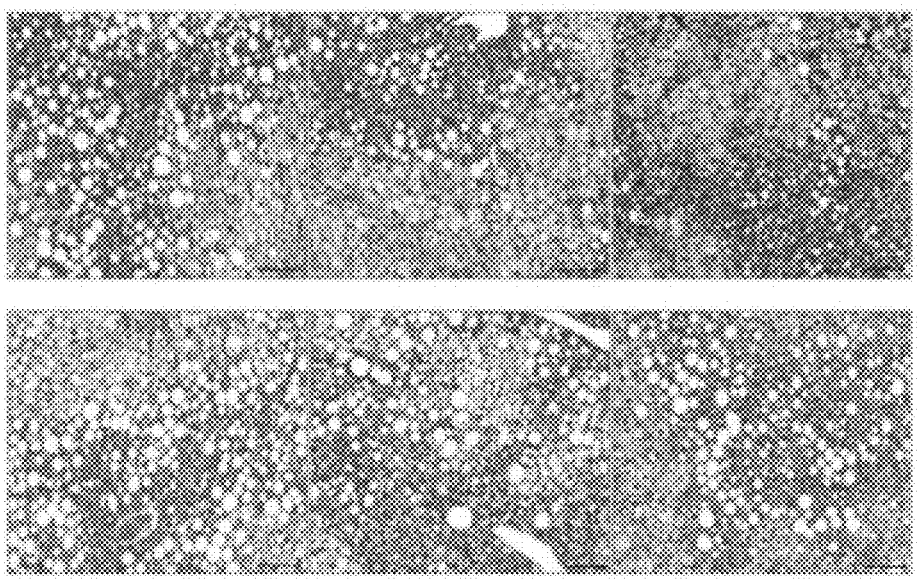
Figure 5C:
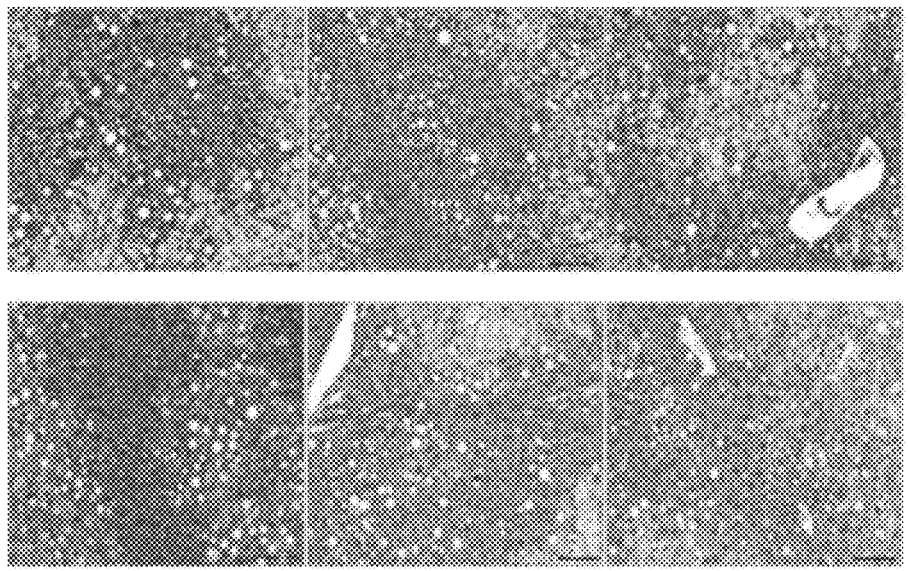
Figure 5D:
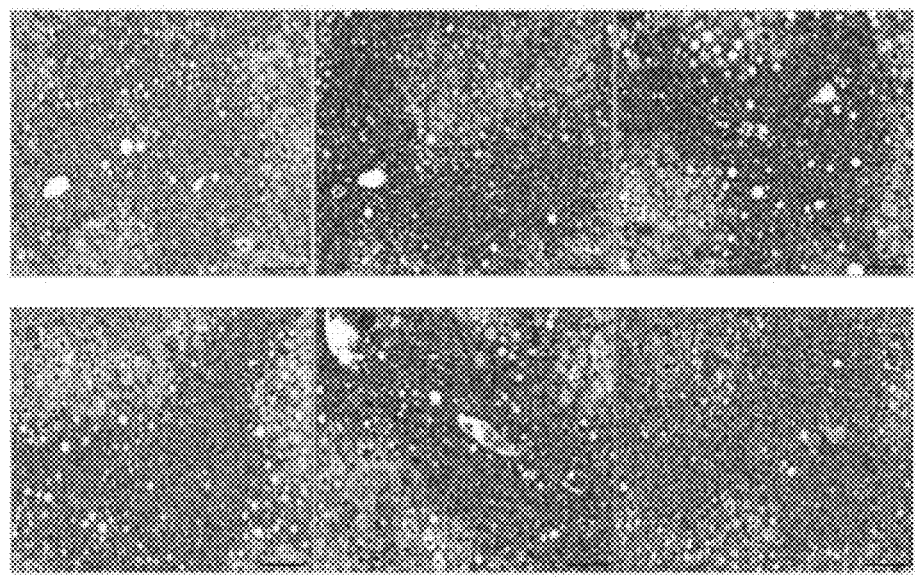
Figure 5E:
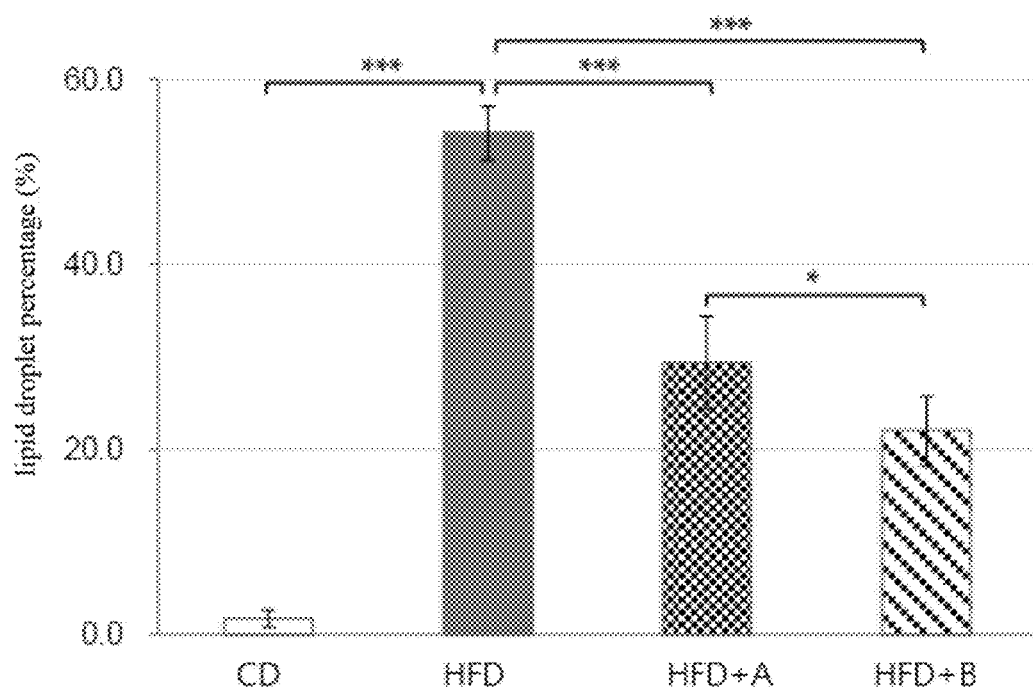
FIG. 5E illustrates percentage of area of lipid droplets relative to the total field of view.

Image J was used to quantify the percentage of area of lipid droplets relative to the total field of view in mice liver tissues (FIG. 5E). It is observed that Group 2 has much higher percentage of area of lipid droplets relative to the total field of view than Group 1, indicating that mice in Group 2 have been induced as the animal model of fatty liver disease. Group 3 and Group 4 were given an intraperitoneal injection of Compound A and Compound B respectively, and these groups have much lower percentage of area of lipid droplets relative to the total field of view than Group 2, with statistical significance, showing that Compound A and Compound B can both alleviate accumulation of hepatic fat induced by high fat diet. Therefore, Compound A and Compound B exemplified in this disclosure have the activity of treating fatty liver disease.

In addition, Group 4 has much lower percentage of area of lipid droplets relative to the total field of view than Group 3, indicating that Compound B is more effective than Compound A in alleviating accumulation of hepatic fat induced by high fat diet.

Example 7: Analysis of Liver Tissue Fibrosis

Figure 6A:
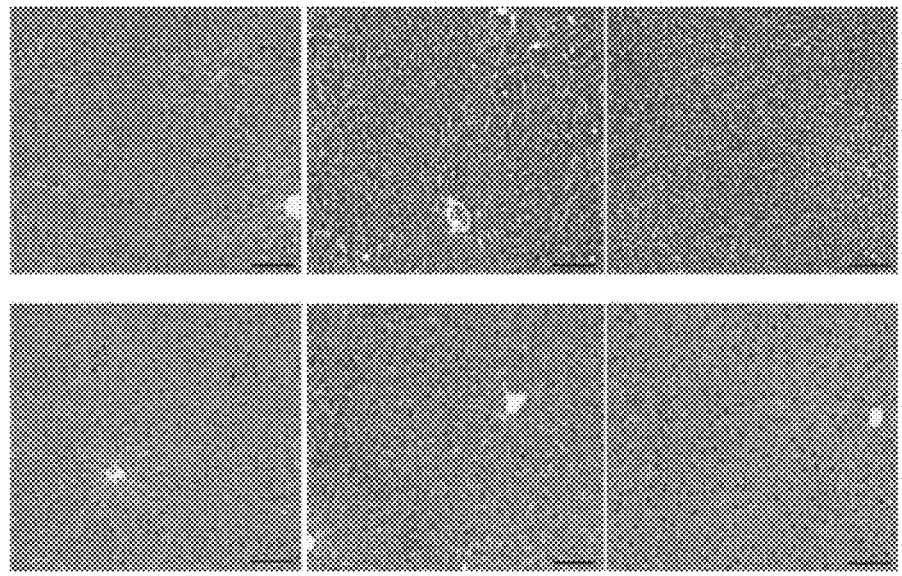
FIG. 6A through FIG. 6D illustrate Masson's Trichrome stain images of liver tissue from each mice group.
Figure 6B:
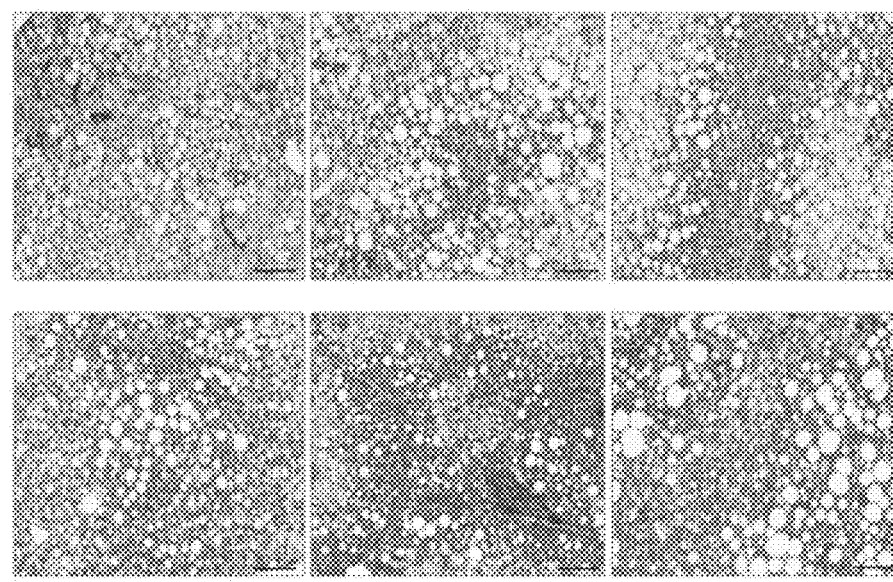
Figure 6C:
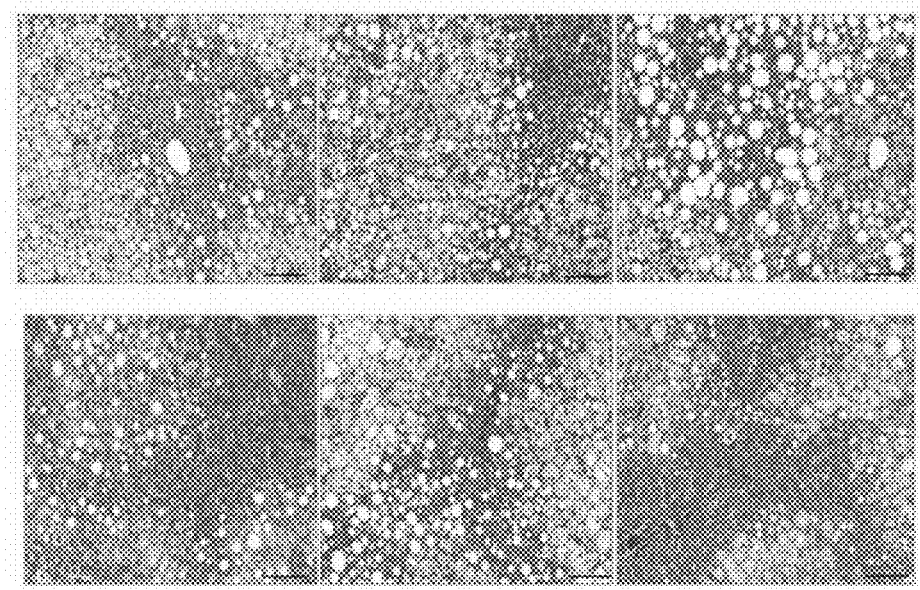
Figure 6D:
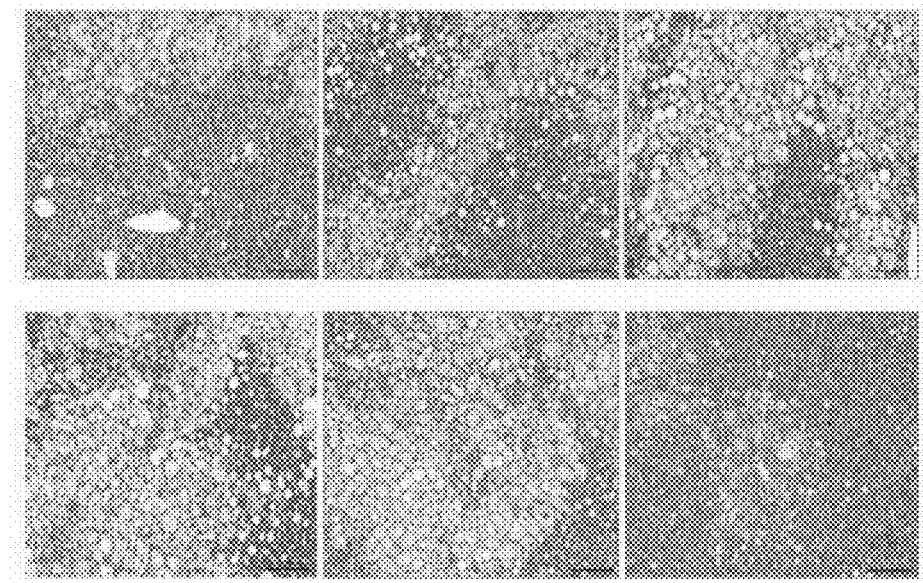

Liver samples from each group in Example 4 obtained at sacrifice were embedded in formalin, sliced and stained with Masson's Trichrome. The results are shown in FIG. 6A (Group 1), FIG. 6B (Group 2), FIG. 6C (Group 3), and FIG. 6D (Group 4), magnification 200×/scale bar 100 µm. Level of accumulation of collagen fiber in liver tissue was observed to evaluate the severity of liver fibrosis. Since severity of liver fibrosis is the most determinant prognostic factor of fatty liver disease, the analysis above may be used to evaluate the effect of high fat diet, Compound A and Compound B on liver fibrosis complicated with fatty liver disease.

| Test Item | Group 1 | Group 2 | Group 3 | Group 4 |
| --- | --- | --- | --- | --- |
| AST (U/L) | 77.3 ± 30.1 | 414.9 ± 182.0** | 200.0 ± 68.4† | 191.3 ± 74.0† |
| ALT (U/L) | 36.1 ± 9.9 | 430.9 ± 165.3*** | 240.5 ± 83.1† | 185.4 ± 83.1†† |
| T-CHO (mg/dl) | 148.1 ± 46.5 | 324.5 ± 57.6*** | 225.3 ± 53.2† | 234.0 ± 33.6†† |
| TG (mg/dl) | 20.5 ± 7.3 | 29.6 ± 14.6 | 30.1 ± 9.8 | 42.2 ± 18.9 |
| GLU (mg/dl) | 260.6 ± 63.7 | 236.1 ± 25.8 | 287.2 ± 60.0 | 274.4 ± 31.0 |

(Six mice in each group; data are represented by mean ± SD; statistical analysis is performed using Student's t test; p-value is illustrated as <0.001 compared with Group 1; *<0.0001 compared with Group 1; †<0.05 compared with Group 2; ††<0.01 compared with Group 2)

Results from the table above indicate that Group 2 has significantly higher measurements in both aspartate transaminase (AST) and alanine transaminase (ALT) than Group 1. Fed with Compound A and Compound B respectively, Group 3 and Group 4 have significantly lower measurements in both aspartate transaminase (AST) and alanine transaminase (ALT) than Group 2, with statistical significance, showing that Compound A and Compound B can both improve abnormal liver function caused by fatty liver.

Example 6: Analysis of Fat Amount in Liver Tissue

Figure 6E:
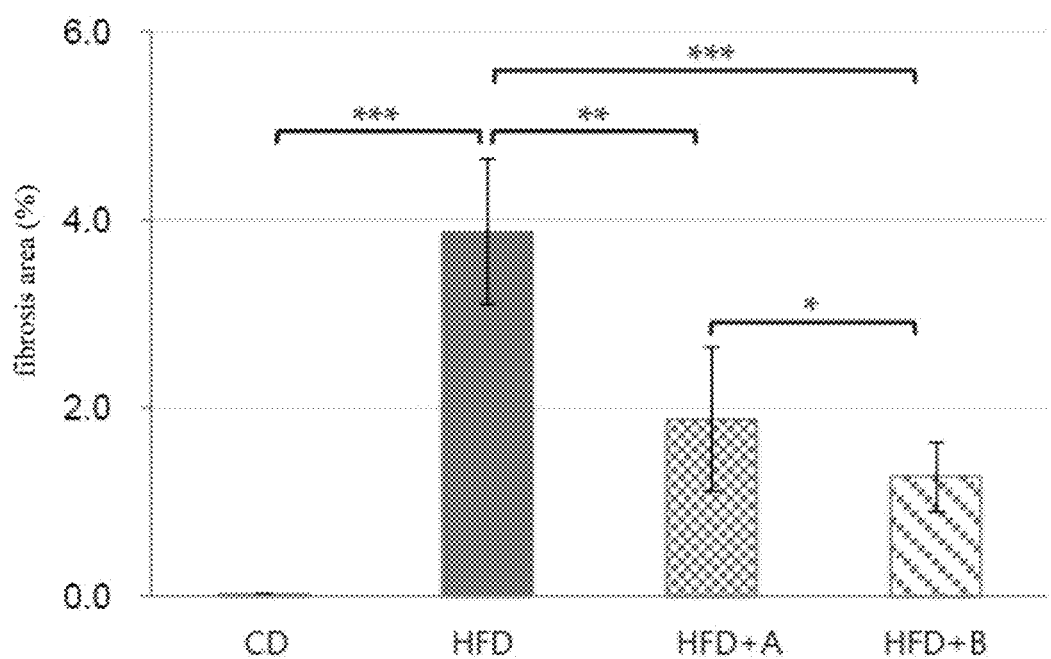
FIG. 6E illustrates percentage of liver tissue fibrosis area following quantitation.

Liver samples from each group in Example 4 obtained at sacrifice were embedded in formalin, sliced and stained with hematoxylin and eosin (H&E). The results are shown in FIG. 5A (Group 1), FIG. 5B (Group 2), FIG. 5C (Group 3), and FIG. 5D (Group 4), magnification 200×/scale bar 100 µm. Since over-accumulation of hepatic fat in liver tissues is the most prominent pathological feature of fatty liver disease, Nuance multispectral image analysis module (PerknElmer, Inc) was used to quantify the collagen proportionate area (CPA), as shown in FIG. 6E. It is observed that Group 1 has very low level of liver tissue fibrosis, while Group 2 has much greater percentage of collagen proportionate area than Group 1, indicating that mice in Group 2 have been induced as the animal model of liver fibrosis complicated with fatty liver disease. Group 3 and Group 4 were given an intraperitoneal injection of Compound A and Compound B respectively, and these groups have much lower percentage of collagen proportionate area than Group 2, both with statistical significance. This indicates that Compound A and Compound B can both alleviate liver fibrosis complicated with fatty liver induced by high fat diet. Therefore, Compound A and Compound B exemplified in this disclosure have the activity of treating liver fibrosis caused by fatty liver disease.

In addition, Group 4 has much lower percentage of fibrosis area than Group 3, indicating that Compound B is more effective than Compound A in alleviating liver fibrosis complicated with fatty liver induced by high fat diet.

Example 8: Effect of Compound C on Lipid Droplet Formation in HepG2 Cells

Compound C, which is a derivative of Compound A, was also tested to further investigate the effect of glucosamine peptide compounds defined herein, including Compound A and its derivatives, on the formation of intracellular lipid droplets. Similar to Example 2, to induce in vitro fatty liver cell model on HepG2 with oleic acid, HepG2 cells were cultured in a 24-well plate at a cell volume of $8 \times 10^4$ and added with 0.1 mM of oleic acid for 24-hour culturing. After the replacement of culture medium containing oleic acid, 10 nM of Compound A and 10 nM of Compound C were individually added to different DMEMs for culturing for 24 hours, and four repetitions were performed for both Compound A and Compound C. ORO staining was used to confirm the level of lipid droplets in HepG2, and their number and size were quantified by Image J.

Figure 7A:
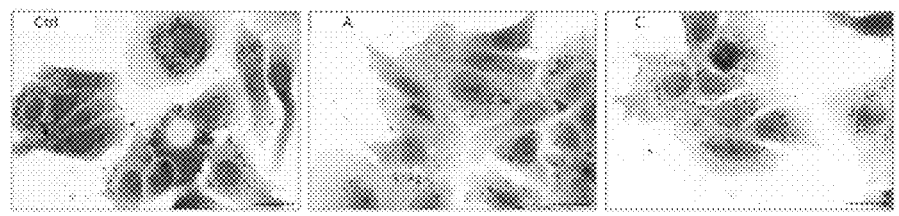
FIG. 7A illustrates images of stained HepG2 cells treated by Compound A or Compound C.
Figure 7B:
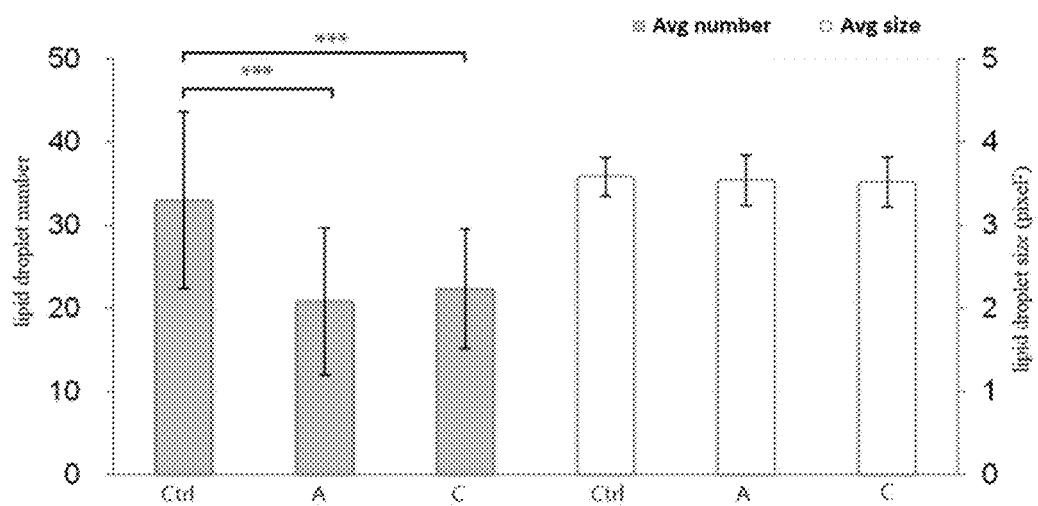
FIG. 7B illustrates bar charts comparing number and size of lipid droplets.

The results show that after 24-hour of treatment with either Compound A or Compound C, lipid droplet accumulation in HepG2 is reduced significantly (FIG. 7A—scale bar: 20 μm, magnification: 1000×, 100× oil objective). Quantification by Image J of the number and size of lipid droplets in HepG2 stained with ORO also shows statistical significance (FIG. 7B).

Accordingly, it is believed that glucosamine peptide compounds disclosed herein can effectively alleviate hepatic fat accumulation and liver fibrosis in mammalian animals with fatty liver induced by high fat diet. Since there is no known cure so far for diseases associated to lipid metabolic disorders of liver, such as fatty liver, the subject matter disclosed herein is useful for treating liver metabolic disorders of human, which has high medical value and commercial potential and is widely applicable to products and therapies for treating liver metabolic disorders.

The above detailed description is merely illustrative in nature and is not intended to limit the embodiments of the subject matter or the application and uses of such embodiments. As used herein, the term "exemplary" means "serving as an example, instance, or illustration." Any implementation described herein as exemplary is not necessarily to be construed as preferred or advantageous over other implementations. In addition, while several representative compounds have been specifically disclosed herein, such as Compounds A to C, it is believed that other compounds or derivatives with the same skeleton (e.g., modified or non-modified acetyl-Glc-lactoyl-AA1-AA2 compounds or acetyl-Glc-lactoyl-AA1-AA2-AA3 compounds or their derivatives) and with similar biological mechanism or pathway (e.g., via NOD2 pathway) can also be reasonably reached by this disclosure and inferred to have similar bioactivity.

Moreover, while at least one exemplary example or comparative example has been presented in the foregoing detailed description, it should be appreciated that a vast number of variations exist. It should also be appreciated that the exemplary one or more embodiments described herein are not intended to limit the scope, applicability, or configuration of the claimed subject matter in any way. Rather, the foregoing detailed description will provide those skilled in the art with a convenient guide for implementing the described one or more embodiments. Also, the scope defined by the claims includes known equivalents and foreseeable equivalents at the time of filing this patent application.

What is claimed is:

1. A method of alleviating fatty liver disease, hepatic steatosis or liver fibrosis induced by high fat diet comprising administering to a subject in need thereof an effective amount of a glucosamine peptide compound or a pharmaceutically acceptable salt thereof;

wherein the glucosamine peptide compound has a structure of Glc-L-Pep, and wherein Glc is a glucosamine moiety, L is a linker, Pep is a peptide moiety consisting of two to six amino acid residues, Glc and L are bonded by an ether linkage, and L and Pep are bonded by an amide linkage, wherein the glucosamine moiety has an amino group acylated to form an amide bond, and wherein the effective amount is determined by measuring or by imaging reduction of lipid droplets to 30 percent of area relative to the total field of view.

2. The method of claim 1, wherein the acyl group has a substitution of $C_1$-$C_{12}$ alkyl or $C_6$-$C_{10}$ aryl.

3. The method of claim 1, wherein one or more hydroxyl groups of the glucosamine moiety is amino-modified, thio-modified, glycoside-modified, glucosamine-modified or acylated.

4. The method of claim 1, wherein -L- is

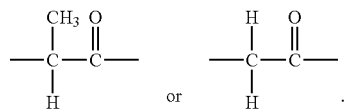

5. The method of claim 1, wherein Pep is a peptide moiety consisting of two or three amino acid residues.

6. The method of claim 1, wherein Pep has a substitution of a lipophilic group.

* * * * *